(12) United States Patent
Ginther et al.

(10) Patent No.: US 9,696,356 B2
(45) Date of Patent: *Jul. 4, 2017

(54) APPARATUS AND METHODS FOR TESTING OF ACOUSTIC DEVICES AND SYSTEMS (71) Applicant: General Electric Company, Schenectady, NY (US)

(72) Inventors: James Ginther, Boulder, CO (US); John Timms, Longmont, CO (US); G. Wayne Moore, Lyons, CO (US); James Gessert, Loveland, CO (US)

(73) Assignee: General Electric Company, Schnectady, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/205,703

(22) Filed: Jul. 8, 2016

(65) Prior Publication Data

US 2016/0320439 A1 Nov. 3, 2016

Related U.S. Application Data

(63) Continuation of application No. 14/340,638, filed on Jul. 25, 2014, now Pat. No. 9,392,387, which is a
(Continued)

(51) Int. Cl.
*G01R 27/26* (2006.01)
*G01R 27/02* (2006.01)
(Continued)

(52) U.S. Cl.
CPC ......... *G01R 27/02* (2013.01); *G01N 29/2437* (2013.01); *G01R 27/2605* (2013.01);
(Continued)

(58) Field of Classification Search
CPC ...... A61M 37/0092; A61M 2037/0007; A61K 41/0047; G01N 27/9046; G01N 29/09;
(Continued)

(56) References Cited

U.S. PATENT DOCUMENTS 3,854,323 A   12/1974 Hearn et al.
4,013,905 A * 3/1977 Breneman .............. G01N 29/14
                                                        310/336
(Continued)

OTHER PUBLICATIONS

United States Patent and Trademark Office, "Non-Final Office action", issued in connection with U.S. Appl. No. 13/081,238, mailed on May 7, 2013, 12 pages.
(Continued)

*Primary Examiner* — Vinh Nguyen
(74) *Attorney, Agent, or Firm* — Hanley, Flight and Zimmerman, LLC (57) ABSTRACT

Methods and devices are disclosed for testing an acoustic probe having transducing elements for converting between acoustic and electrical signals. An electrical signal is generated at a frequency with a testing device capable of generating electrical signals over a range of frequencies. The electrical signal is transmitted to at least some of the transducing elements to measure a complex impedance and thereby evaluate a performance of the transducing elements.

20 Claims, 7 Drawing Sheets

Related U.S. Application Data continuation of application No. 13/081,238, filed on Apr. 6, 2011, now Pat. No. 8,803,532.

(51) Int. Cl.
*H04R 29/00* (2006.01)
*G01R 31/02* (2006.01)
*G01N 29/24* (2006.01)

(52) U.S. Cl.
CPC .............. *G01R 31/02* (2013.01); *H04R 29/00* (2013.01); *H04R 29/005* (2013.01); *G01N 2291/018* (2013.01); *H04R 2420/09* (2013.01)

(58) Field of Classification Search
CPC .. G01N 29/2462; G01N 29/30; G01N 29/348; G01N 2291/014; G01N 27/10; G01N 29/11; G01N 29/2487; G01N 29/28; G01N 29/46; G01N 33/48707; G06F 17/30539; H04R 2499/13; H04R 29/003; H04R 5/04; H04R 29/00; H04R 3/00; H04R 3/12; H04S 7/301; H04S 7/308; G01H 15/00; G01R 25/00; G01R 27/02; G02F 1/33; H03H 7/40
See application file for complete search history.

(56) References Cited

U.S. PATENT DOCUMENTS

| | | | |
|---|---|---|---|
| 6,470,996 B1 * | 10/2002 | Kyle | G01V 1/46 181/103 |
| 7,007,539 B2 | 3/2006 | Gessert et al. | |
| 7,398,166 B2 | 7/2008 | Stirnemann | |
| 7,726,172 B2 | 6/2010 | Moore et al. | |
| 8,803,532 B2 | 8/2014 | Ginther et al. | |
| 2004/0213417 A1 | 10/2004 | Gessert et al. | |
| 2009/0326609 A1 | 12/2009 | Doron | |
| 2015/0008942 A1 | 1/2015 | Ginther et al. | |

OTHER PUBLICATIONS

United States Patent and Trademark Office, "Final Office action", issued in connection with U.S. Appl. No. 13/081,238, mailed on Jan. 8, 2014, 12 pages.

United States Patent and Trademark Office, "Notice of Allowance", issued in connection with U.S. Appl. No. 13/081,238, mailed on Apr. 3, 2014, 7 pages.

United States Patent and Trademark Office, "Non-Final Office action", issued in connection with U.S. Appl. No. 14/340,638, mailed on Sep. 4, 2015, 17 pages.

United States Patent and Trademark Office, "Notice of Allowance", issued in connection with U.S. Appl. No. 14/340,638, mailed on Mar. 11, 2016, 18 pages.

\* cited by examiner

APPARATUS AND METHODS FOR TESTING OF ACOUSTIC DEVICES AND SYSTEMS

RELATED APPLICATION

This patent arises from a continuation of U.S. patent application Ser. No. 14/340,638, filed Jul. 25, 2014, entitled "APPARATUS AND METHODS FOR TESTING OF ACOUSTIC DEVICES AND SYSTEMS", which claims priority to U.S. patent application Ser. No. 13/081,238, filed Apr. 6, 2011, entitled "APPARATUS AND METHODS FOR TESTING OF ACOUSTIC DEVICES AND SYSTEMS", both of which are hereby incorporated herein by reference in their entireties.

BACKGROUND OF THE INVENTION

This application relates generally to acoustic probes. More specifically, this application relates to apparatus and methods for testing acoustic probes.

Acoustic imaging techniques are valuable in a wide range of applications. While the most notable are undoubtedly medical applications in the form of ultrasound imaging, acoustic techniques are more generally used at a variety of different acoustic frequencies for imaging a variety of different phenomena. For example, acoustic imaging techniques may be used for the identification of structural defects and for detection of impurities, in addition to taking advantage of the nonionizing character of ultrasound radiation for imaging living biological bodies. Just some of the medical applications for acoustic imaging include the imaging of fetuses being carried by pregnant women, the detection of tumors in various organs of the body, particularly in soft-tissue structures, and the imaging of organs when real-time information is the preferred method for diagnostic functions with echocardiography.

All of these techniques rely fundamentally on the fact that different structures, whether they be biological or otherwise, have different acoustic impedances. When acoustic radiation is incident on an acoustic interface, such as where the acoustic impedance changes discontinuously because of the presence of a tumor in an organ, it may be scattered in ways that permit characterization of the interface. Radiation reflected by the interface is most commonly detected in such applications, but there are certain ultrasound scanning methodologies that additionally or alternatively make use of transmitted radiation.

Transmission of the acoustic radiation towards a target and receipt of the scattered radiation may be performed and/or coordinated with a modern acoustic imaging system. Many modern systems are based on multiple-element array transducers that may have linear, curved-linear, phased-array, or similar characteristics. These transducers may, for example, form part of an acoustic probe coupled with the acoustic system to perform the actual acoustic measurements. In some instances, the imaging systems are equipped with internal self-diagnostic capabilities that allow limited verification of system operation, but do not generally provide effective diagnosis of the transmission and receiving transducer elements that make up the probe itself. Degradation in performance of these elements is often subtle and occurs as a result of extended transducer use and/or through user abuse. Acoustic imaging systems therefore often lack any direct quantitative method for evaluating probe performance.

There is accordingly a general need in the art for apparatus and methods for testing acoustic probes.

SUMMARY

Embodiments of the invention provide methods of testing an acoustic probe having a plurality of transducing elements for converting between acoustic and electrical signals. A first electrical signal is generated at a first frequency with a testing device capable of generating electrical signals over a range of frequencies. The first electrical signal is transmitted to selected ones of the plurality of transducing elements. A first respective complex impedance is measured with the first electrical signal for each of the selected ones of the plurality of transducing elements. A performance of the each of the selected ones of the plurality of transducing elements is evaluated from the first respective complex impedance.

Such evaluation may include determining a capacitance from the first respective complex impedance, such as when the first frequency is not a resonant frequency of the each of the selected ones of the plurality of transducing elements. Alternatively, such an evaluation may include determining a resistance from the first respective complex impedance, such as when the first frequency is a resonant frequency of the each of the selected ones of the plurality of transducing elements. The resonant frequency may be specified by receiving an identification of the acoustic probe, and receiving a specification of the resonant frequency in accordance with the identification of the acoustic probe to define the first frequency. The evaluation may also alternatively comprise determining both a capacitance and a resistance from the first respective complex impedance.

In some embodiments, a second electrical signal is generated at a second frequency different from the first frequency with the testing device. The second electrical signal is transmitted to the selected ones of the plurality of transducing elements. A second respective complex impedance is measured with the second electrical signal for the each of the selected ones of the plurality of transducing elements. The performance of the each of the selected ones of the plurality of transducing elements thus comprises evaluating the performance of the each of the selected ones of the plurality of transducing elements from the first and second respective complex impedances.

In certain of these embodiments, the first frequency is not a resonant frequency of the each of the selected ones of the plurality of transducing elements while the second frequency is substantially the resonant frequency of the selected ones of the plurality of transducing elements. A capacitance may be determined from the first respective complex impedance and a resistance may be determined from the second respective complex impedance. Alternatively, a first capacitance and a first resistance may be determined from the first respective complex impedance and a second capacitance and a second resistance may be determined from the second respective complex impedance.

The first frequency may in some instance be a predetermined frequency not dependent on an identification of the acoustic probe.

These methods may be embodied by a testing device having a body, a coupling interface, a processor, and impedance circuitry. The coupling interface is integrated with the body and adapted for connection with the acoustic probe. The impedance circuitry is internal to the body and coupled with the processor. The processor is coupled with the coupling interface and capable of generating electrical signals over a range of frequencies and has instructions to implement the methods and described above.

The processor may comprise a direct digital synthesizer.

The body may be sized and shaped to be portable. In addition, the body may have a generally arcuate shape that includes a handle adapted to interlace with a handle on an acoustic system coupled with the acoustic probe.

Specification of the resonant frequency in those embodiments that use it may be simplified when the testing device further comprises a storage device coupled with the processor so that the processor may additionally include instructions to retrieve the specification of the resonant frequency from the storage device. Also, the testing may sometimes further comprise a camera integrated with the body and coupled with the processor, which additionally includes instructions to operate the camera to read information from a label associated with the acoustic probe.

BRIEF DESCRIPTION OF THE DRAWINGS

A further understanding of the nature and advantages of the present invention may be realized by reference to the remaining portions of the specification and the drawings, wherein like reference labels are used through the several drawings to refer to similar components.

DETAILED DESCRIPTION OF EXEMPLARY EMBODIMENTS

Embodiments of the invention provide methods and apparatus for testing acoustic probes that make use of measurements of complex impedance. Such acoustic probes generally comprise a plurality of acoustic transducers to effect conversion between electrical and acoustic forms of energy. Typically, the transducers comprise piezoelectric crystals that deform in response to application of voltage. Sound may thus be generated with transducers configured as transmitter elements through the application of periodically varying voltage to cause mechanical oscillation, and thereby acoustic waves, at particular frequencies. Similarly, transducers may be configured as receiver elements so that periodic deformations that result from the impingement of acoustic waves induce the generation of a voltage that can be detected, measured, and/or used in applications.

While much of the discussion below specifically discusses apparatus and methods that are suitable for testing ultrasonic probes, this is intended merely for exemplary purposes; the invention is not intended to be limited by the operational frequency characteristics used by the tested probes. Testing of acoustic probes as described herein allows a broad range of defects to be identified, including not only irregularities in connection issues but also identification of acoustic issues like lens delamination, array malfunctions, and other issues that interfere with optimal functioning of the probe. As is evident from the description below, this is possible because changes in the acoustic coupling of a transducer are manifested in its electrical impedance, permitting the acoustic anomalies to be determined as long as the impedance measurement is sufficiently accurate.

Figure 1:
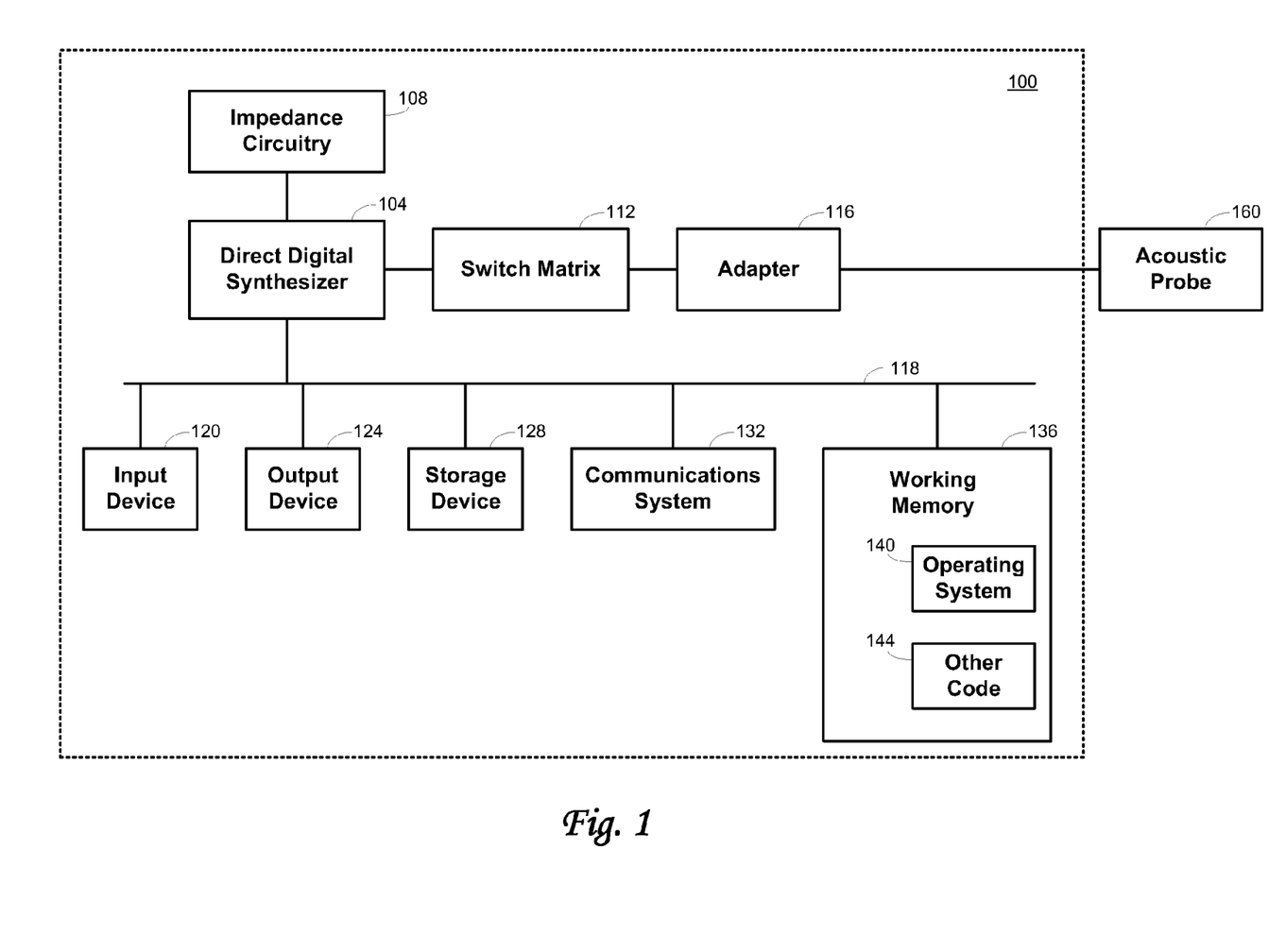
FIG. 1 is a block diagram illustrating a functional structure for a device that may be used in embodiments of the invention to test an acoustic probe.

FIG. 1 provides a broad functional overview of a test device 100 in accordance with embodiments of the invention. An acoustic probe 160 may be tested when coupled with the test device 100 through the generation of signals to provide a broadband pulse that excites all the transducer elements of the probe 160. The signals may be generated with a direct digital synthesizer ("DDS") 104, which is a type of frequency synthesizer capable of creating arbitrary waveforms from a reference clock. As is known in the art, the DDS 104 may generate waveforms over a range of frequencies by using a numerically controlled oscillator that relies on the reference clock to provide a stable time base and thereby produce a discrete quantized version of the desired waveform, with a period controlled by a digital word contained in a frequency control register. Embodiments of the invention typically use sinusoidal waveforms over a frequency range of about 10 kHz-20 MHz, although other frequency ranges may be used in a variety of alternative embodiments, such as 100 kHz-15 MHz, 200 kHz-10 MHz, or 500 kHz-5 MHz. The desired frequency range of the DDS 104 corresponds to a range suitable to test a variety of different acoustic probes 160 produced by different manufacturers, which may have different resonant frequencies. The range of 10 kHz-20 MHz is appropriate to test a wide range of commercially available probes that are currently produced, but those of skill in the art will readily appreciate that other ranges may be used to accommodate testing of a more limited or more expanded set of commercially available acoustic probes. Alternative waveform generators may be used in other embodiments. For example, an analog generator such as a phase-locked loop might be used, although such analog alternatives typically have reduced frequency agility, increased phase noise, and less-precise control over the output phase across frequency switching transitions.

The signal generated by the DDS 104 is routed to selected ones or a subset of transducing elements comprised by the acoustic probe 160 being tested by a switch matrix 112 and perhaps also an adapter 116. The ability to use low voltages in measuring the impedance advantageously allows electronic switches to be used by the switch matrix 112 in one embodiment, reducing the size of the unit when compared with the use of alternative electromechical relays. In cases where a signal is routed simultaneously to a subset group of the transducing elements, the subset group may correspond to a group of neighboring transducing elements. The switch matrix 112 comprises a bidirectional switching array capable of establishing the desired connections. It is generally desirable for electrical characteristics of the switch matrix 112 not to impact the evaluation of the transducing elements. Accordingly, an array of miniature relays may be preferred in some embodiments over semiconductor-based switching integrated circuitry to limit capacitive and resistive loads. The relays may be arranged in groups to limit the number of traces that may be active at any given time. In addition, a regular circuit topology may be used to keep the electrical load substantially constant. In one embodiment, a correction factor determined uniquely for each element may be used to further reduce measurement errors that may be associated with electrical loading associated with the switch matrix 112.

The switch matrix 112 may be considered to perform a mapping from one channel that corresponds to the DDS 104 to a plurality of channels that are in communication with the probe 160. In some instances, particularly in embodiments that use solid-state switches, probes of many different manufacturers that make use of the some connector, such as the ITT Cannon DL series, may be connected directly with the test device 100. Probes of other manufacturers that use different physical configurations, such as pinless or cartridge connectors, may be coupled to the test device with an adapter 116. In some embodiments, the adapter 116 is configured to provide a 1:1 mapping from transducing elements of the probe 160 to channels of the switch matrix 112. Thus, for example, if the probe has 192 transducing elements, the adapter 116 may map each of 192 channels from the switch matrix 112 to one of the transducing elements. In other embodiments, the adapter 116 may instead be configured to provided different schemes for mapping channels from the switch matrix 112 to transducing elements of the probe 160.

Impedance circuitry 108 coupled with the DDS 104 enables the test device 100 to measure the complex impedance of the probe elements as coupled through the switch matrix 112 and adapter 116 at frequencies established by the DDS 104 in accordance with known probe characteristics. This is described in further detail below.

The DDS 104 may also be coupled with other elements of the testing device 100, with the drawing illustrating how such individual elements may be implemented in a separated or more integrated manner. In particular, the testing device 100 is shown comprised of hardware elements that are electrically connected with the DDS 104 via bull 18, including an input device 120, an output device 124, a storage device 128, and a communications system 132. The communications system 132 may comprise a wired, wireless, modem, and/or other type of interfacing connection and permits data to be exchanged with external devices as desired.

The testing device 100 may also comprise software elements, shown as being currently located within working memory 136, including an operating system 140 and other code 144, such as a program designed to implement methods of the invention. It will be apparent to those skilled in the art that substantial variations may be made in accordance with specific requirements. For example, customized hardware might also be used and/or particular elements might be implemented in hardware, software (including portable software, such as applets), or both. Further, connection to other computing devices such as network input/output devices may be employed. Connections between the testing device 100 may thus use any suitable connection, such as a parallel-port connection, a universal-serial-bus ("USB") connection, and the like.

Figure 2A:
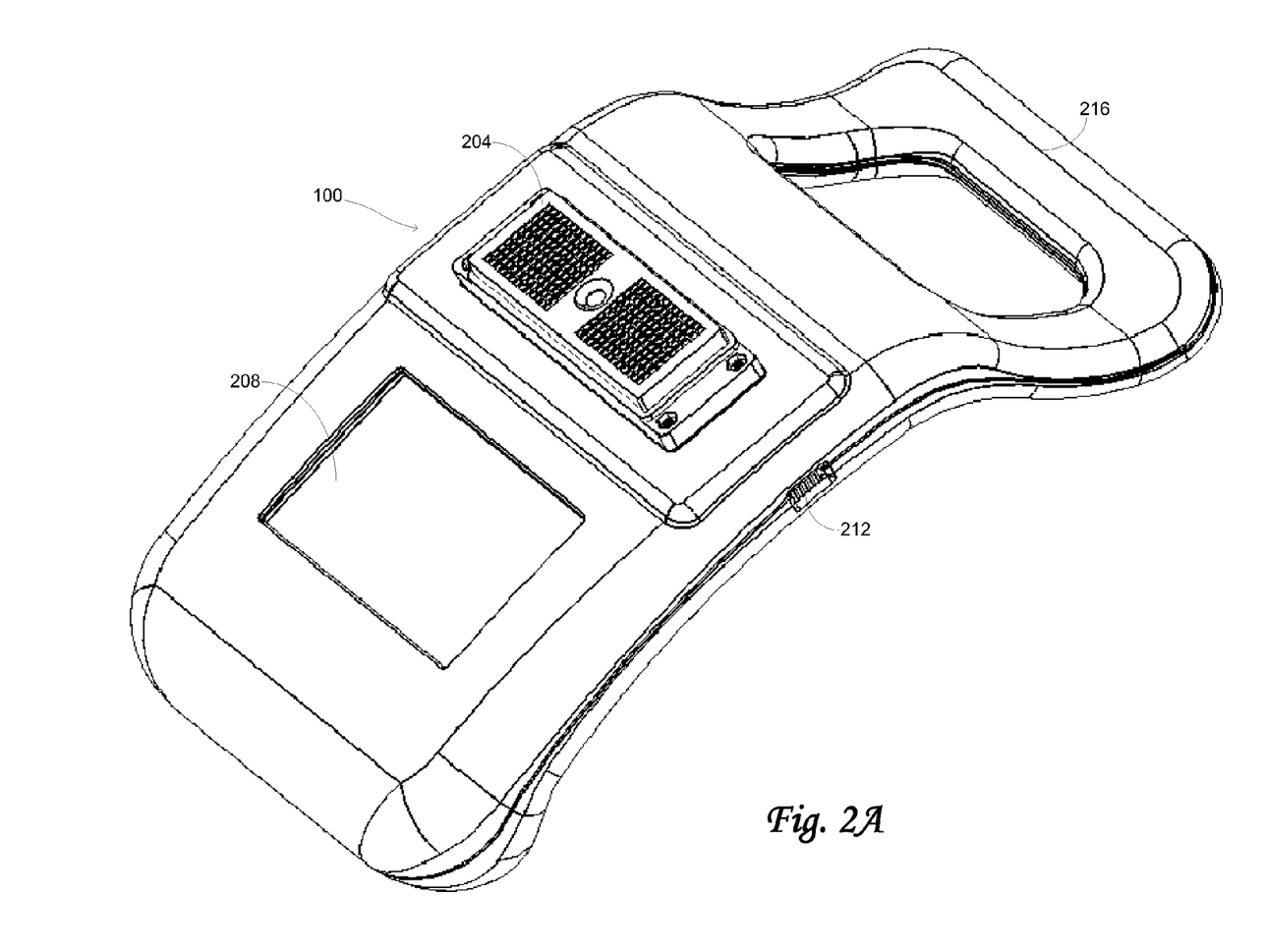
FIGS. 2A, 2B, and 2C respectively provide structural front, and side views of the device illustrated functionally in FIG. 1.
Figure 2B:
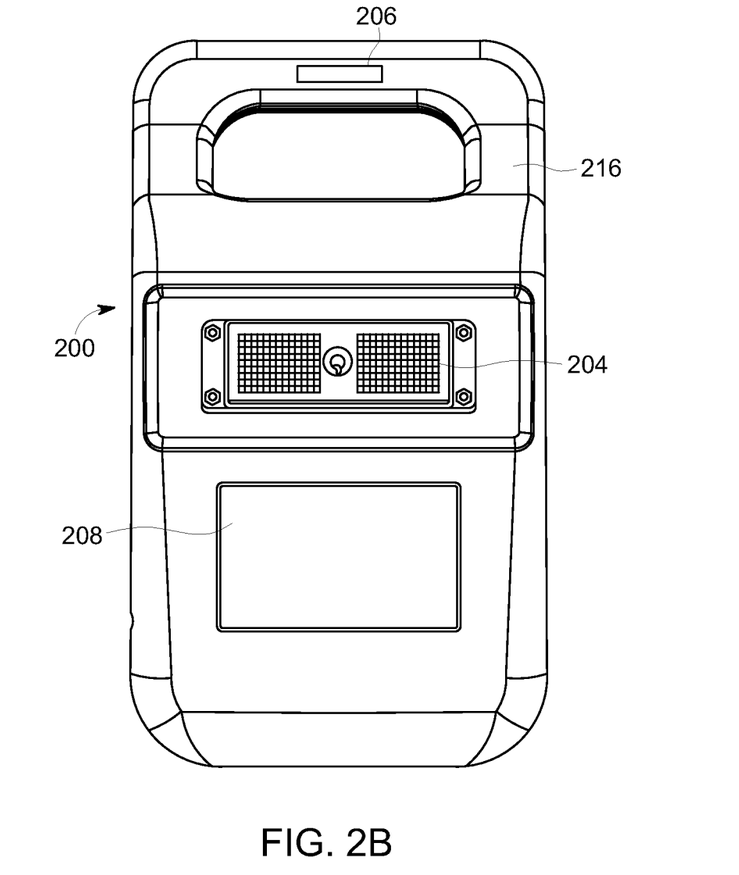
Figure 2C:
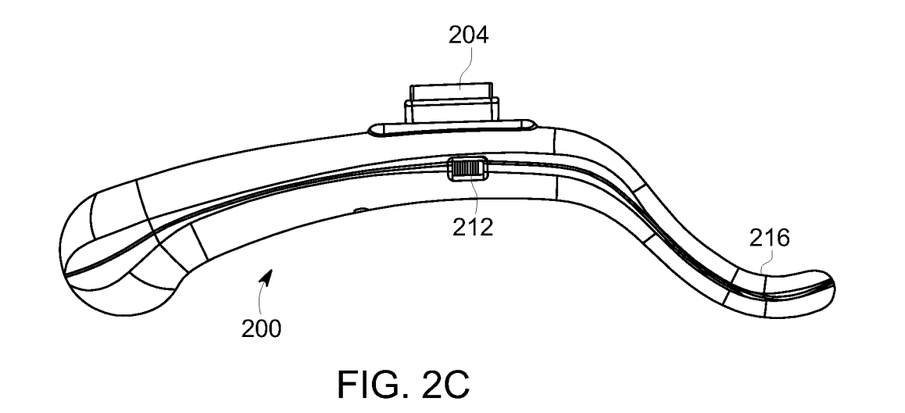

An example of a physical structure for the testing device 100 is illustrated in perspective, front, and side views respectively in FIGS. 2A, 2B, and 2C. The structure in these views is merely exemplary and many other structures may be used, but the illustrated embodiment highlights some features that may generally be included in the physical structure of the testing device 100. For example, the device 100 shown in FIGS. 2A-2C is sized so as to be easily carried by hand, and includes a handle 216 to facilitate such carrying. In some embodiments, the handle 216 may include slots (not shown) on a reverse side, allowing the device 100 conveniently to be hung on a wall near while the probe 160 is being tested. The handle 216 may also be adapted to interlace with a handle on an acoustic system coupled with the probe 160 being tested. As evident most clearly from the side view of FIG. 2C, the device 100 may also have a generally arcuate shape in which the handle 216 and bottom of the device 100 act as legs to support the device 100 when it is rested on a flat surface like a table or floor. The arcuate shape is preferred over a flat shape because it presents a display screen 208 comprised by the device 200 in a position where in may be more easily consulted by an operator. The display screen 208 may function as the output device 124 shown functionally in FIG. 1, and in embodiments in which the display screen 208 comprises a touch screen may additionally function as the input device 120 shown functionally in FIG. 1.

The device 100 may also include a camera 206 that may also correspond to the input device 120 in the functional drawing of FIG. 1. Such a camera 206 enables capturing an image associated with the acoustic probe 160 to be studied. Such an image may record information about the probe 160, which may be determined by a variety of different mechanisms. In one embodiment, for example, the camera 206 may be used to read a label from the acoustic probe 160 that identifies the probe 160 with such information as the identity of the probe manufacturer, a model number, and the like. Such identification information may be provided directly as part of the label or the label may provide a reference identifier that may be cross-referenced with identification information stored in the storage device 128 or in a remote storage accessible with the communications system 132. Label information may be read using any of a variety of techniques known in the art, including the use of character-recognition or barcode-reading techniques. In embodiments where barcode labels are used, any appropriate barcode symbology may be used, including one-dimensional and two-dimensional symbologies. Examples of one-dimensional symbologies include Codabar, Code 11, Code 128, Code 32, Code 39, Code 93, EAN-13, EAN-8, EAN-99, EAN-Velocity, Industrial 2 of 5, Interleaved 2 of %, ISBN, UPC-A, UPC-E, and other symbologies. Examples of two-dimensional symbologies include Aztec Code, Code 16K, PDF417, Compact PDF417, Micro PDF417, Macro PDF417, DataMaxtrix, QR Code, Semacode, and other formats. In addition, embodiments of the invention may accommodate both monochromatic and color barcode symbologies, including, for example, the High Capacity Color Barcode ("HCCB") symbology.

In addition to these features, the device 100 includes a coupling interface 104 for connection to the system to be tested and may also include one or more communications ports 212 for wired interconnection with computational or other devices. The communications ports 212 may be coupled with the communications system 132 of FIG. 1 and may take any appropriate configuration, including USB, Firewire, serial, parallel, PS/2, SCSI, and other types of communications ports. Alternative to the wired interconnection is wireless interconnection, which may be implemented using any secured or unsecured wireless communications protocol known in the art.

Figure 3:
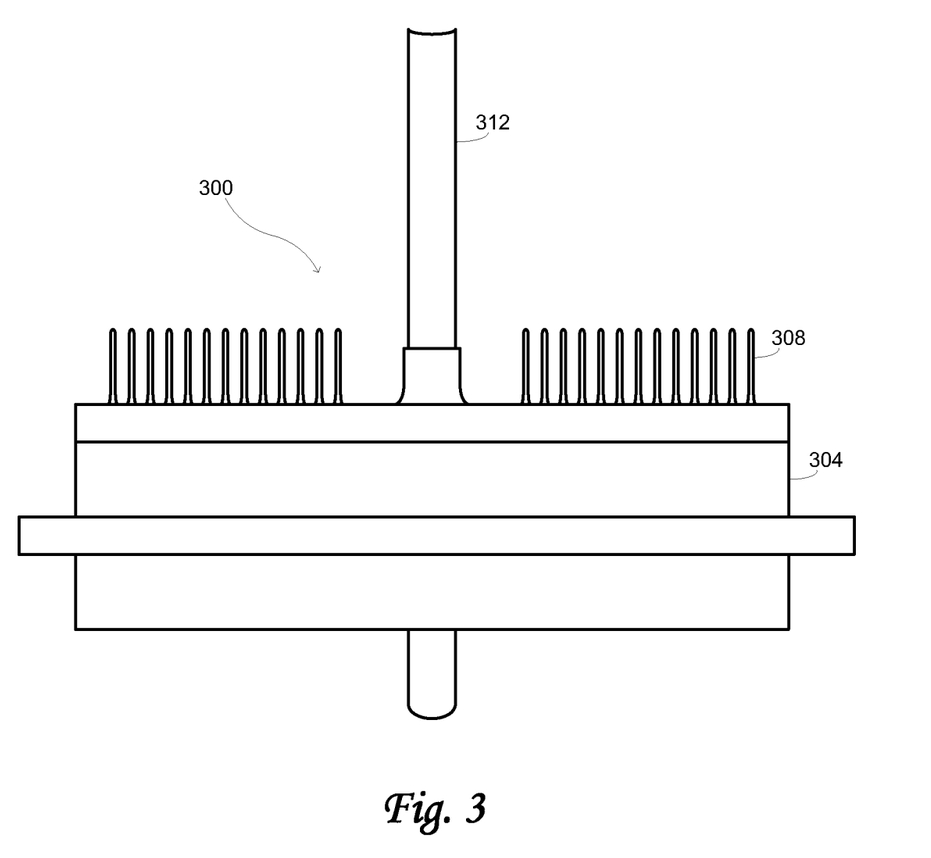
FIG. 3 illustrates a structure for a probe adapter that may be used in some embodiments to interface a probe with the testing device.

The coupling interface 204 is particularly adapted to integrate with an acoustic probe 160 and may correspond to the adapter 116 shown functionally in FIG. 1. Advantageously, the coupling interface 204 may be configured for integration with a variety of different probe structures. In one embodiment, for instance, the coupling interface 204 is configured for interfacing with a physical-configuration connector such as the ITT Cannon DL series of connectors. An example of such a connector is illustrated with FIG. 3. The connector 300 includes a body 304, a shaft 312, and a plurality of retractable pins. The connector 300 may be coupled with a probe 160 using the shaft 312, with contact by a number of the pins 308 varying in accordance with the size and shape of the probe 160. Particularly with such a connector 300, the coupling interface 204 enables the device 100 to test probes from many manufacturers without the need for additional individual adapters.

Figure 4A:
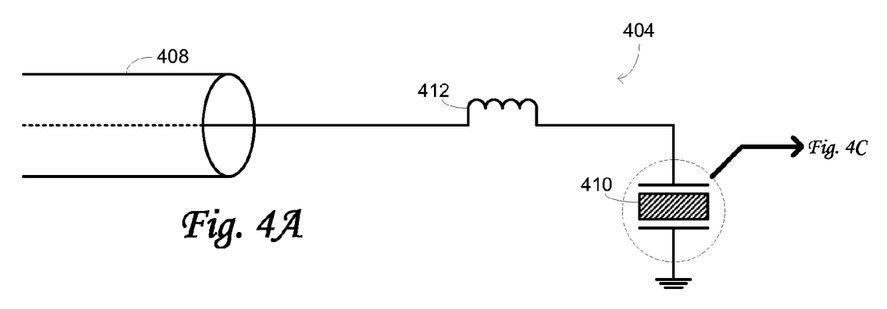
FIGS. 4A and 4B illustrate series and parallel tuning arrangements of an acoustic probe.
Figure 4B:
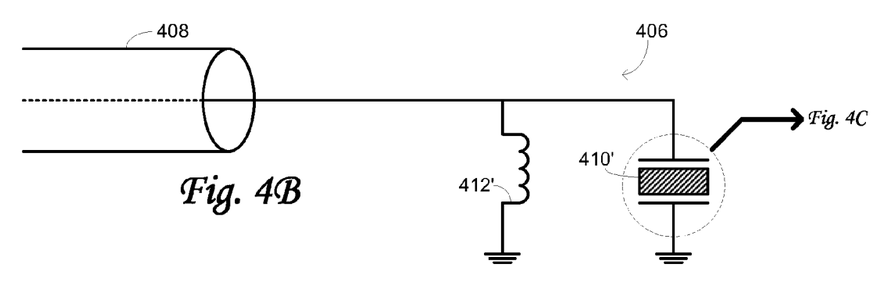
Figure 4C:
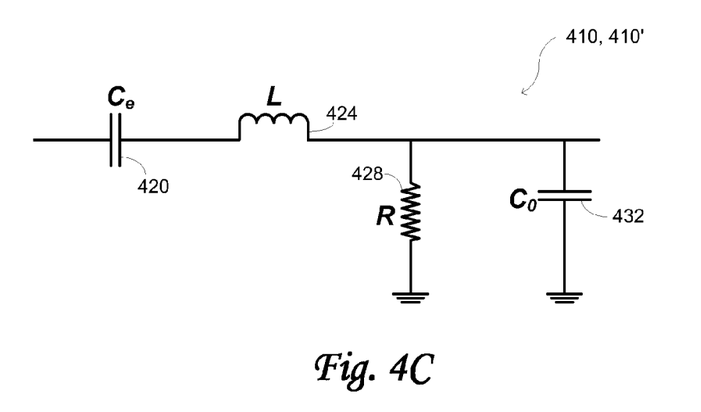
FIG. 4C is an example of an electronic model of an acoustic transducer.

The relevant electrical structure for probe transducers is illustrated in FIGS. 4A-4C. The complex impedance of each of the transducing element may be determined through interrogation of that element by generating a waveform at one or more appropriate frequencies with the DDS 104 and measuring the response of the impedance circuitry 108. In some instances, this method may be complicated by a probe structure that provides a significant contribution to the imaginary part of the complex impedance in the form of an additional source of capacitance. In particular, each transducing element may comprise a piezoelectric crystal used to perform the electrical-acoustic conversions. The probe may supply energy to each such piezoelectric crystal with a coaxial cable that has an intrinsically high capacitance. Probe manufacturers accordingly often use a tuning circuit to tune out the capacitance of the coaxial cable and thereby permit effective energy coupling into the piezoelectric crystal. Any suitable tuning circuit known to those of skill in the art may be used, such as with a standard second-order tuned circuit. The tuning circuit typically comprises an inductive element, which may be provided in series or in parallel with the piezoelectric crystal. Methods of the invention may account for the specific configuration of the tuning circuit in different embodiments.

FIG. 4A, for example, shows the electrical structure of a series-inductor tuned probe 404 in which energy is coupled into the piezoelectric crystal 410 comprised by each transducing element with a coaxial cable 408. The circuit for tuning out the capacitance of the coaxial cable 408 comprises an inductive element 412 provided in series with the piezoelectric crystal 410, and may also include a resistive element (not shown), usually provided in parallel with the piezoelectric crystal 410. FIG. 4B similarly shows the electrical structure of a parallel-inductor tuned probe 406. In this instance, the tuning circuit comprises an inductive element 412' provided in parallel with the piezoelectric crystal 410', and may also include a resistive element (not shown), usually also provided in parallel with the piezoelectric crystal 410'.

Testing of both series-inductor tuned probes may thus be performed in a manner similar to that used for an untuned probe. In particular, the DDS 104 may provide waveforms at appropriate frequencies to enable the complex impedance to be determined with the impedance circuitry 108. The series-inductor tuned probe 404 generally permits even lower frequencies to be used than does the parallel-inductor tuned probe 406 because very-low-frequency waveforms may generate a small inductive reactance with the parallel-inductor tuned probe 406. In either instance, though a frequency may be chosen that is outside the active range of the piezoelectric crystal 410, 410' to avoid spurious interference with operation of the probe. In particular, frequencies may be used that are below the resonance frequency of the piezoelectric crystal 410, 410'. Typically used piezoelectric crystals have resonant frequencies in the range of 2-20 MHz and while it is possible to use a different off-resonance frequency determined individually for each probe, this is not necessary and impedance measurements may be made at the same frequency for each probe. In some embodiments, the off-resonance frequency is a predetermined frequency in the range of 0.5-1.5 MHz, such as at 1.0 MHz.

FIG. 4C provides an electrical model of the piezoelectric transducer 410 or 410'. It is noted that this is one of a number of different electrical models that may be used but is adequate to illustrate the electrical behavior of the testing device 100 as it interacts with acoustic probes. The voltage across the crystal is proportional to the intensity of the acoustic signals generated or received by the crystal. The inductance L 424 corresponds to the seismic mass and inertia of the sensor itself. The capacitance $C_e$ 420 is inversely proportional to the mechanical elasticity of the sensor and the capacitance $C_0$ 432 represents the static capacitance of the transducer, resulting from an inertial mass of infinite size. Of particular interest is the resistance R 428, which corresponds to the leakage resistance of the transducer element. An infinite value of R in the model indicates that there is no energy leakage, a configuration that may be achieved with the off-resonance frequencies discussed above.

Measurements of the complex impedance according to embodiments of the invention captures all of the electrical information represented with the model, enabling a variety of different types of performance issues to be diagnosed. Determination of a capacitance from the complex impedance permits a number of potential connection issues to be evaluated. For example, capacitance determinations may be used to identify defects associated with the coaxial cables used to couple energy to the respective piezocrystals. The capacitance is a particularly useful discriminant for this type of diagnosis because it is approximately proportional to the distance along the cable where a defect occurs. If interrogation of a particular transducing element results in no capacitive part of the complex impedance, the respective cable may not be connected with that transducing element. If interrogation of that transducing element instead results in a capacitive part of the complex impedance that is a fraction of what is otherwise expected for a properly functioning transducing element, the respective cable may be broken or otherwise damaged at a point along its length that corresponds to the fractional capacitance value.

Figure 5A:
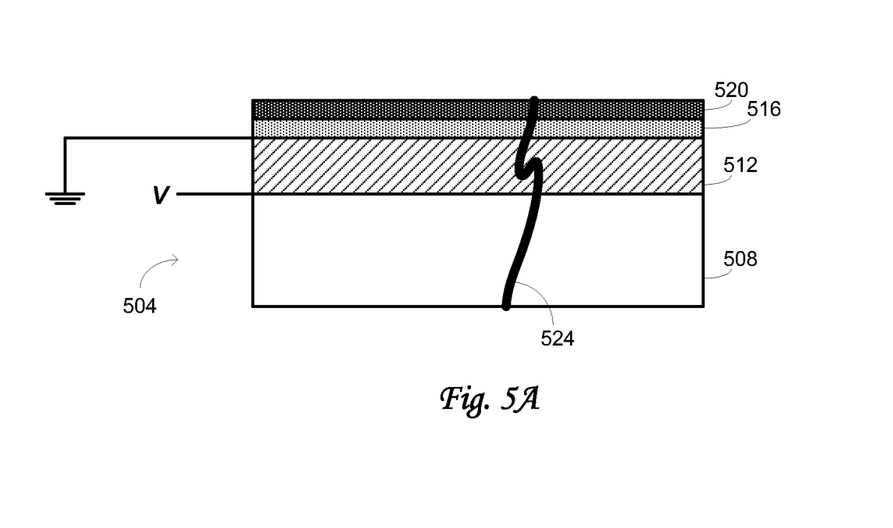
FIG. 5A provides a schematic illustration of a structure for an acoustic transducer.

Other information that may be determined from the capacitive part of the complex impedance is more limited. FIG. 5A provides an example of a physical structure of a transducer element 504. It comprises a backing 508 over which the piezoelectric crystal 512 itself is provided. An acoustic lens 516 over the piezoelectric crystal 512 provides electrical isolation of the piezoelectric crystal 512 as well as acoustic impedance matching, and may be covered with a metal layer 520 such as a layer of gold. While issues such as delamination of the acoustic lens 516 from the piezoelectric crystal 512 or the presence of a crack 524 or similar damage to the piezoelectric crystal 512 may be suggested by the capacitive component of the complex impedance, the resistive part of the impedance provides greater diagnostic information. For example, a lack of electrical signal is suggestive of both conditions, with a concomitant capacitance matching with fully functioning transducer elements suggesting lens delamination and a concomitant mismatch suggesting damage to the piezoelectric crystal 512.

A second complex-impedance measurement at resonance enables determination of a resistive component since the resistance R 428 in the model of FIG. 4C then takes a finite value that can be compared with an expected resistance characteristic of a functioning transducer. Even in circumstances where an electrical signal exists, a deviation in the resistance provides diagnostic information of a defect in the transducer that may not be available from capacitance information alone. For example, for some probes the resolution is too small for a capacitance measurement to give adequate information for reliable diagnosis of a defect. The full information available from the complex impedance permits verification both that the transducer element is properly connected and that it is behaving as expected for a functioning transducer.

Figure 5B:
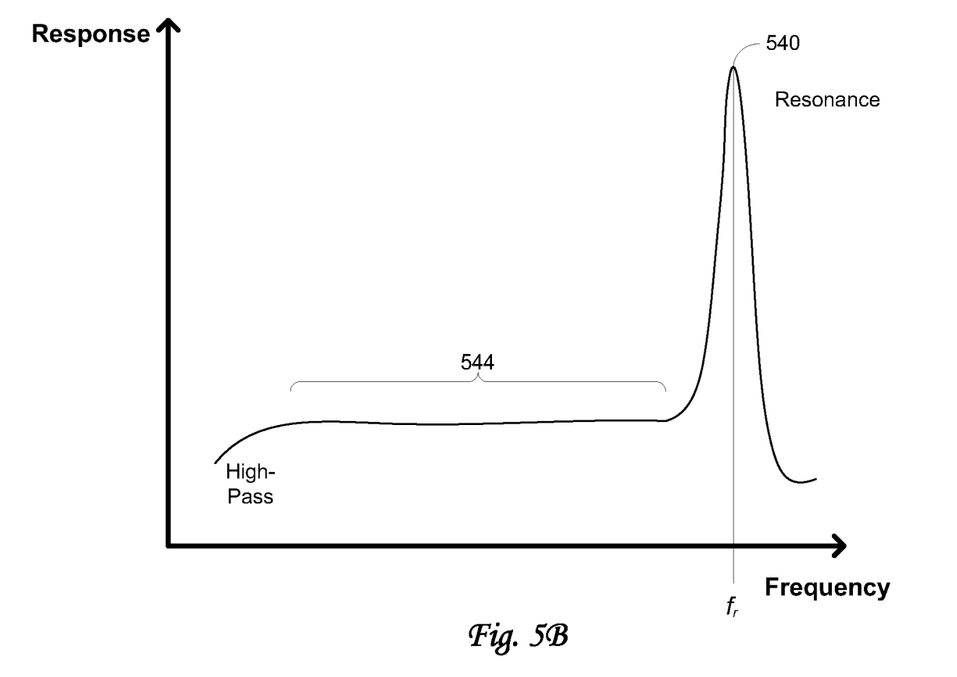
FIG. 5B provides a simplified illustration of the frequency response of an acoustic transducer for purposes of illustration.

This may be better understood with reference to FIG. 5B, which simplifies the frequency response of a piezoelectric sensor for purposes of illustration. Between the high-pass cutoff and the resonant peak 540, there is a substantially flat region 544 that is normally used operationally. A measurement of the complex impedance in this flat region 544 combined with a measurement at the resonance frequency permits considerably enhanced diagnostic information to be extracted. The expected resistance at resonance may depend on the particular characteristics of the probe being tested. Accordingly, a set of acceptable resistance ranges may be stored for each probe type the testing device 100 is configured to test, either locally at the storage device 128 of the testing device 100 itself or remotely so that such ranges are accessible to the testing device 100 with the communications system 132. The acceptable range may depend not only on the specific probe type, but also on the array itself and perhaps also on the loading.

Deviation of the resistance outside the acceptable range is particularly useful for diagnosis of issues with the transducer itself. For example, if the piezoelectric crystal 512 is cracked as illustrated in FIG. 5A, the effective size of the element is reduced, driving the resistance R 428 to a value that represents less energy coupling and also less energy loss in the piezoelectric element.

Figure 6:
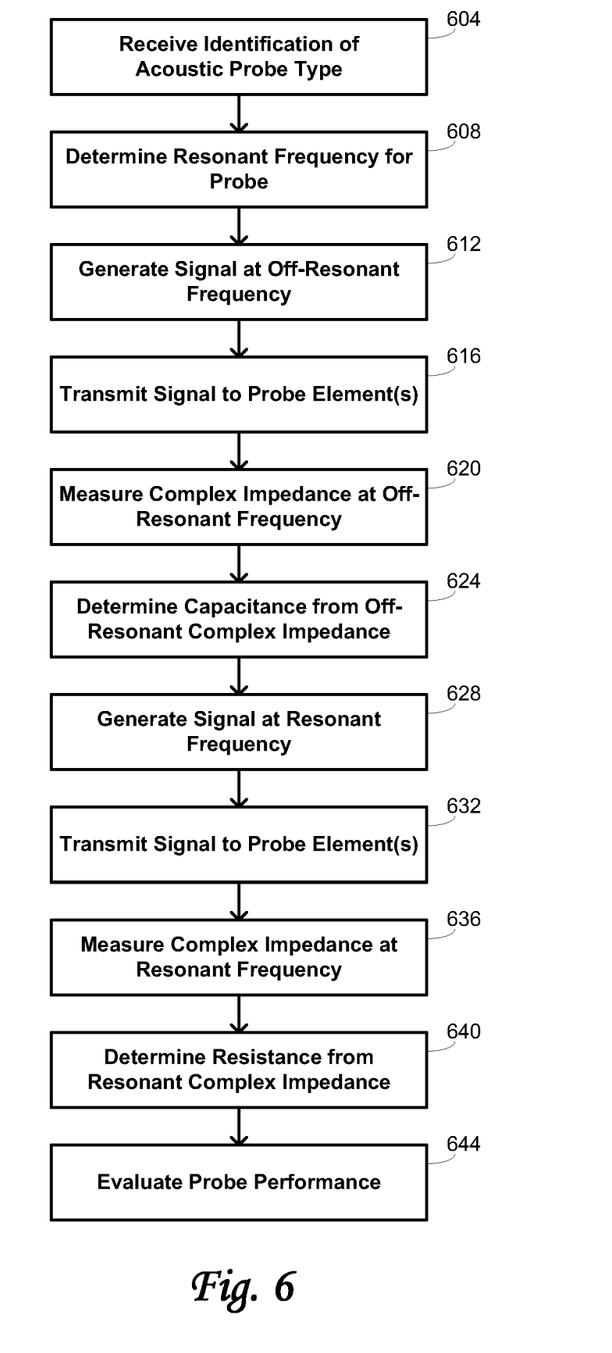
FIG. 6 is a flow diagram summarizing methods of testing acoustic probes in accordance with embodiments of the invention.

Methods of the invention are accordingly summarized with the flow diagram of FIG. 6. While the flow diagram sets out specific steps in a specific order, this is merely intended to be illustrative. More generally, there are embodiments within the scope of the invention in which certain of the identified steps are omitted, embodiments in which additional steps not specifically identified are performed, and embodiments in which some of the steps are performed in a different order than appears in the drawing. For example, while the flow diagram includes complex-impedance measurements both on- and off-resonance, such multiple measurements are not necessary in all embodiments and the complex impedance might be determined at only a single frequency.

The method begins at block 604 by receiving an identification of the acoustic probe type. This information may be received by the testing device in any of several ways. For example, the camera 206 might be used to read a barcode or other type of label. Alternatively, a technician operating the testing device 100 might use the input device 120 in the form of a touchscreen or otherwise to enter an identification of the probe type. The identification of the probe type at block 604 is relevant because of the capability of the testing device 100 to test a variety of different probes. Such identification specifies a number of parameters that are relevant to interpreting the complex-impedance values determined from measurements performed on the probe. This includes not only the resonant frequency of the probe, which is determined by the testing device 100 from the identification at block 608, but also the acceptable capacitance and resistance values.

At block 612, a signal is generated by the DDS 104 of the testing device 100 at an off-resonant frequency. As previously noted, the frequency used for this signal, which is transmitted to the probe elements at block 616, may conveniently be the same for every probe type by exploiting the fact that there is a limit to the value of the resonance frequency for most commercially available acoustic probes. But in alternative embodiments, the off-resonant frequency value may also depend on probe type.

At block 620, the off-resonance complex impedance is measured. In principle, both the real and imaginary parts of the complex impedance contain diagnostic information, although it is generally expected that the imaginary component corresponding to the capacitance is most useful since the resistance off-resonance diverges. Accordingly, the off-resonance capacitance is determined from the measured complex impedance at block 624.

At block 628, a signal is generated by the DDS 104 at the resonance frequency for the transducers of the particular acoustic probe being tested and is transmitted to the probe elements at block 632. Again, in principle, both the real and imaginary parts of the complex impedance measured at block 636 have diagnostic information that may be used, but the real component that corresponds to the resistance as determined at block 640 is of particular utility.

At block 644, the performance of the probe is evaluated using the collected impedance information, which may include complex impedance values at a plurality of frequencies for each transducing element comprised by the acoustic probe. The ability of the testing device 100 in this way to measure a true complex impedance over a range of frequencies advantageously permits it to be used for the measurement of a variety of different acoustic probes, which may have various tuning circuits, without needing a special adapter. Furthermore, the structure and functionality of the testing device 100 permit the measurements to be taken without the need to provide acoustic coupling with a water bath, gel, or similar material for acoustic-impedance matching. Element switching that is tolerant of high voltage pulses is also unnecessary. Without the need to include a water bath, reflection target, and high-voltage switching, the device may accordingly be configured as described herein as a self-contained, battery-powered, portable unit.

Having described several embodiments, it will be recognized by those of skill in the art that various modifications, alternative constructions, and equivalents may be used without departing from the spirit of the invention. Accordingly, the above description should not be taken as limiting the scope of the invention, which is defined in the following claims.

The invention claimed is:

1. A method of testing an acoustic probe having a transducing element for converting between acoustic and electrical signals, the method comprising:
    generating, with a testing device, an electrical signal at a first frequency;
    transmitting the electrical signal to the transducing element of the acoustic probe;
    measuring, with the testing device, a complex impedance of the transducing element in response to the electrical signal; and evaluating a performance of the transducing element based on A) the complex impedance of the transducing element and B) an identification of a type of the acoustic probe.

2. The method of claim 1, further including:
capturing an image associated with the acoustic probe; and
identifying the type of the acoustic probe based on the captured image.

3. The method of claim 2, wherein the identification of the type of acoustic probe is based on at least one of a barcode or a label of the acoustic probe captured in the image.

4. The method of claim 1, wherein the identification of the type of the acoustic probe corresponds to an acceptable impedance range for the transducing element.

5. The method of claim 1, wherein the evaluating of the performance of the transducing element based on the complex impedance includes determining a capacitive part associated with the complex impedance with the testing device.

6. The method of claim 1, wherein the evaluating of the performance of the transducing element based on the complex impedance includes determining a resistive component associated with the complex impedance with the testing device.

7. The method of claim 1, wherein the first frequency is substantially a resonant frequency of the transducing element.

8. The method of claim 7, further including retrieving a specification of the resonant frequency based on the identification of the type of the acoustic probe to define the first frequency.

9. The method of claim 1, wherein the electrical signal is a first electrical signal and the complex impedance is a first complex impedance, further including:
generating a second electrical signal at a second frequency different from the first frequency with the testing device;
transmitting the second electrical signal to the transducing element of the acoustic probe; and
measuring a second complex impedance of the transducing element, the evaluating of the performance of the transducing element being based on A) the first and second complex impedances of the transducing element and B) the identification of the type of the acoustic probe.

10. The method of claim 9, wherein:
the first frequency is not a resonant frequency of the transducing element; and
the second frequency is substantially the resonant frequency of the transducing element.

11. A testing device for testing an acoustic probe having a transducing element for converting between acoustic and electrical signals, the testing device comprising:
a direct digital synthesizer to:
generate an electrical signal at a first frequency; and
transmit the electrical signal to the transducing element of the acoustic probe; and
impedance circuitry to measure a complex impedance of the transducing element in response to the electrical signal, wherein at least one of the direct digital synthesizer or the impedance circuitry evaluates a performance of the transducing element based on A) the complex impedance of the transducing element and B) an identification of a type of the acoustic probe.

12. The testing device of claim 11, further including a camera to:
capture an image associated with the acoustic probe; and
identify the type of the acoustic probe based on the captured image.

13. The testing device of claim 12, wherein the identification of the type of acoustic probe is based on at least one of a barcode or a label of the acoustic probe captured in the image.

14. The testing device of claim 11, wherein the identification of the type of the acoustic probe corresponds to an acceptable impedance range for the transducing element.

15. The testing device of claim 11, wherein at least one of the direct digital synthesizer or the impedance circuitry is to evaluate the performance of the transducing element based on the complex impedance by determining a capacitive part associated with the complex impedance with the testing device.

16. The testing device of claim 11, wherein the first frequency is substantially a resonant frequency of the transducing element.

17. The testing device of claim 16, wherein at least one of the direct digital synthesizer or the impedance circuitry is to retrieve a specification of the resonant frequency based on the identification of the type of the acoustic probe to define the first frequency.

18. The testing device of claim 11, wherein the electrical signal is a first electrical signal and the complex impedance is a first complex impedance, and:
the direct digital synthesizer is to:
generate a second electrical signal at a second frequency different from the first frequency with the testing device; and
transmit the second electrical signal to the transducing element of the acoustic probe; and
the impedance circuitry is to measure a second complex impedance of the transducing element, wherein at least one of the direct digital synthesizer or the impedance circuitry evaluates the performance of the transducing element based on A) the first and second complex impedances of the transducing element and B) the identification of the type of the acoustic probe.

19. The testing device of claim 18, wherein:
the first frequency is not a resonant frequency of the transducing element; and
the second frequency is substantially the resonant frequency of the transducing element.

20. A tangible computer readable medium comprising instructions which, when executed, cause a processor to at least:
generate an electrical signal at a first frequency;
transmit the electrical signal to a transducing element of an acoustic probe;
measure a complex impedance of the transducing element in response to the electrical signal; and
evaluate a performance of the transducing element based on A) the complex impedance of the transducing element and B) an identification of a type of the acoustic probe.

* * * * *